US008588894B2

(12) United States Patent
Saba et al.

(10) Patent No.: US 8,588,894 B2
(45) Date of Patent: Nov. 19, 2013

(54) DETERMINATION OF SITE OF ORIGIN FOR A NATURAL ELECTRICAL PULSE IN A LIVING BODY

(75) Inventors: Magdi M. Saba, Towson, MD (US); Stephen R. Shorofsky, Owings Mills, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 796 days.

(21) Appl. No.: 12/680,454

(22) PCT Filed: Sep. 25, 2008

(86) PCT No.: PCT/US2008/077708
§ 371 (c)(1),
(2), (4) Date: Mar. 26, 2010

(87) PCT Pub. No.: WO2009/045852
PCT Pub. Date: Apr. 9, 2009

(65) Prior Publication Data
US 2010/0262203 A1  Oct. 14, 2010

Related U.S. Application Data

(60) Provisional application No. 60/976,409, filed on Sep. 28, 2007.

(51) Int. Cl.
*A61N 1/362* (2006.01)

(52) U.S. Cl.
USPC ........... 600/512; 600/508; 600/509; 600/510; 600/515; 600/516; 600/517; 600/518; 607/4; 607/5; 607/9; 607/11; 607/17; 607/25; 607/26; 607/115; 607/119; 607/125; 128/920

(58) Field of Classification Search
USPC .......... 600/508–510, 512, 515–518; 607/1–2, 607/4–5, 9, 11, 17, 25, 26, 115, 119, 125; 128/920
See application file for complete search history.

(56) References Cited

U.S. PATENT DOCUMENTS 5,846,198 A   12/1998  Killmann
6,658,285 B2 *  12/2003  Potse et al. .................... 600/515
(Continued)

FOREIGN PATENT DOCUMENTS

WO    WO 2004-026123 A2    4/2004

OTHER PUBLICATIONS

ISUSA, International Search Report and Written Opinion for the corresponding PCT application PCT/US2008077708, Apr. 19, 2012, pp. 1-7.

(Continued)

*Primary Examiner* — Deborah Malamud
(74) *Attorney, Agent, or Firm* — Evans & Molinelli, PLLC; Eugene J. Molinelli

(57) ABSTRACT

Techniques include determining a first vector of temporal changes in electrical data measured at multiple electrical sensors positioned at corresponding locations on a surface of a living body due to a natural electrical pulse. A different vector of temporal changes in electrical data measured at the same electrical sensors is determined due to each stimulated signal of multiple stimulated signals within the living body. Stimulated position data is received, which indicates a different corresponding position within the living body where each of the stimulated signals originates. The site of origin of the natural electrical pulse is determined based on the first vector and the multiple different vectors and the stimulated position data. Among other applications, these techniques allow the rapid, automatic determination of the site of origin of ventricular tachycardia arrhythmia (VT).

13 Claims, 7 Drawing Sheets

(56) References Cited

U.S. PATENT DOCUMENTS

| | | | |
|---|---|---|---|
| 6,760,622 B2 * | 7/2004 | Helland et al. | 607/9 |
| 2002/0038093 A1 | 3/2002 | Potse et al. | |
| 2007/0060829 A1 | 3/2007 | Pappone | |

OTHER PUBLICATIONS

International Search Report, PCT/US2008/077708, Sep. 25, 2008, pp. 1-3.

* cited by examiner

DETERMINATION OF SITE OF ORIGIN FOR A NATURAL ELECTRICAL PULSE IN A LIVING BODY

CROSS-REFERENCE TO RELATED APPLICATIONS

This present application is a national phase application of PCT Application No. PCT/US2008/077708, filed on Sep. 25, 2008 and claims priority to Provisional Appln. 60/976,409, filed Sep. 28, 2007, the entire contents of which are hereby incorporated by reference as if fully set forth herein, under 35 U.S.C. §119(e).

BACKGROUND OF THE INVENTION

1. Field of the Invention

The present invention relates to detecting a site of origin of a natural electrical pulse inside a living body, such as a ventricular tachycardia arrhythmia (VT).

2. Description of the Related Art

Sudden cardiac death (SCD) afflicts an estimated 450,000 people annually in United States alone. Ninety percent of these events are related to structural heart disease, of which ischemic heart disease represents the majority. Loss of functioning myocardium through infarction leads to a decline in ventricular function and congestive heart failure, and provides the substrate for malignant ventricular tachyarrhythmias.

The recognition that depressed left ventricular systolic function secondary to myocardial infarction dramatically increases the risk of SCD led to the design and execution of several, large, multicenter, randomized trials over the past 15 years the results of which collectively showed a survival benefit conferred by the implantation of an implantable cardioverter-defibrillator (ICD) compared to optimal medical therapy alone. The ICD is now indicated for the primary prevention of SCD in patients with depressed left ventricular systolic function and symptoms of heart failure, and for secondary prevention in patients who have been resuscitated from an episode of SCD.

Ventricular tachycardia (VT) is a frequently-lethal arrhythmia arising from the ventricles that is most commonly associated with cardiac disease, mainly ischemic heart disease and idiopathic cardiomyopathy. With the advent and widespread use of the ICD, many patients are successfully treated for such malignant ventricular tachyarrhythmias, which would have been otherwise fatal. However, as such patients survive these events, both the incidence and prevalence of patients with recurrent ICD shocks for VT are increasing. Strategies to control VT include anti-arrhythmic medications and ablative therapy. The findings of the classic drug trials, specifically CAST, where anti-arrhythmic drugs were administered to suppress complex ventricular ectopy in post-myocardial infarction patients, were disturbing. Such drugs, namely the class I anti-arrhythmic drugs, were associated with increased, not decreased, mortality. It is now contraindicated to use this class of drugs in patients with structural heart disease. Therefore, there is a restricted choice of anti-arrhythmic drugs to use, with limited efficacy and considerable side effect profiles, in an increasing population of patients with VT who are receiving recurrent ICD shocks. Trial results have shown that ICD shocks are associated with increased patient morbidity, hospitalizations, and mortality.

The mechanical interruption of VT circuits in the left ventricular myocardium was first practiced by surgeons guided by cardiac electrophysiologists as subendocardial resection of scarred tissue and aneurysmectomy. Catheter-based techniques soon evolved, due to increasing demand. Currently the ablation of VT is almost solely performed in the electrophysiology laboratory by a cardiac electrophysiologist using a variety of energy sources, such as chemical, thermal, electrical and optical, and mainly by radiofrequency waves and low-temperature (cryo-ablation). However, myriad factors contrive to make catheter ablation of VT the most challenging electrophysiologic al procedure for a patient to undergo and an electrophysiologist to undertake. In its current state, catheter ablation for VT is indicated as important adjunctive therapy in patients with symptomatic VT in combination with the ICD and anti-arrhythmic drugs.

The most time-consuming step in the VT ablation procedure is the identification of its site of origin (SO). Considerable experience is required to conduct the rapid visual inspection and comparison of multiple electrocardiographs (ECGs) followed by rapid catheter manipulation to successive sites during pace-mapping. In pace-mapping, a stimulated electric pulse is introduced to the myocardium at a specific site using a catheter and the depolarization pulse propagation is monitored on 12 leads of a standard ECG. Automated matching of pace-maps and the VT ECG can be performed by existing software to determine when the myocardium has been stimulated at the VT SO. But, when the myocardium is stimulated at a site other than the VT SO, the matching software provides no data on the VT SO or any guidance as to where to stimulate or otherwise direct attention next to bracket or converge on the VT SO. Currently, there is no available automated technique that would guide the operator toward the VT SO.

SUMMARY OF THE INVENTION

Techniques are provided for determining a site of origin of a natural electrical pulse in a living body.

In one set of embodiments, a method includes determining a first vector of temporal changes in electrical data measured at multiple electrical sensors positioned at corresponding locations on a surface of a living body due to a natural electrical pulse. A different vector of temporal changes in electrical data measured at the same electrical sensors is determined due to each stimulated signal of multiple stimulated signals within the living body. Stimulated position data is received, which indicates a different corresponding position within the living body where each of the stimulated signals originates. The site of origin of the natural electrical pulse is determined based on the first vector and the multiple different vectors and the stimulated position data.

In other sets of embodiments, an apparatus or system or computer readable medium is configured to perform one or more steps of the above method.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Techniques are described for determining the site of origin for a natural electrical pulse inside a living body. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are descried below in the context of determining a site of origin for VT using conventional ECG leads and an electrical ablating probe at the tip of a catheter. However, the invention is not limited to this context. In other embodiments the site of origin of other electrical pulses inside a living body are determined using the same or different surface electrical sensors and probe or probes. For example, in some embodiments, more or fewer ECG electrodes placed at standard or non-standard positions on the surface of a human body are used.

1.0 Structural Overview

Figure 1:
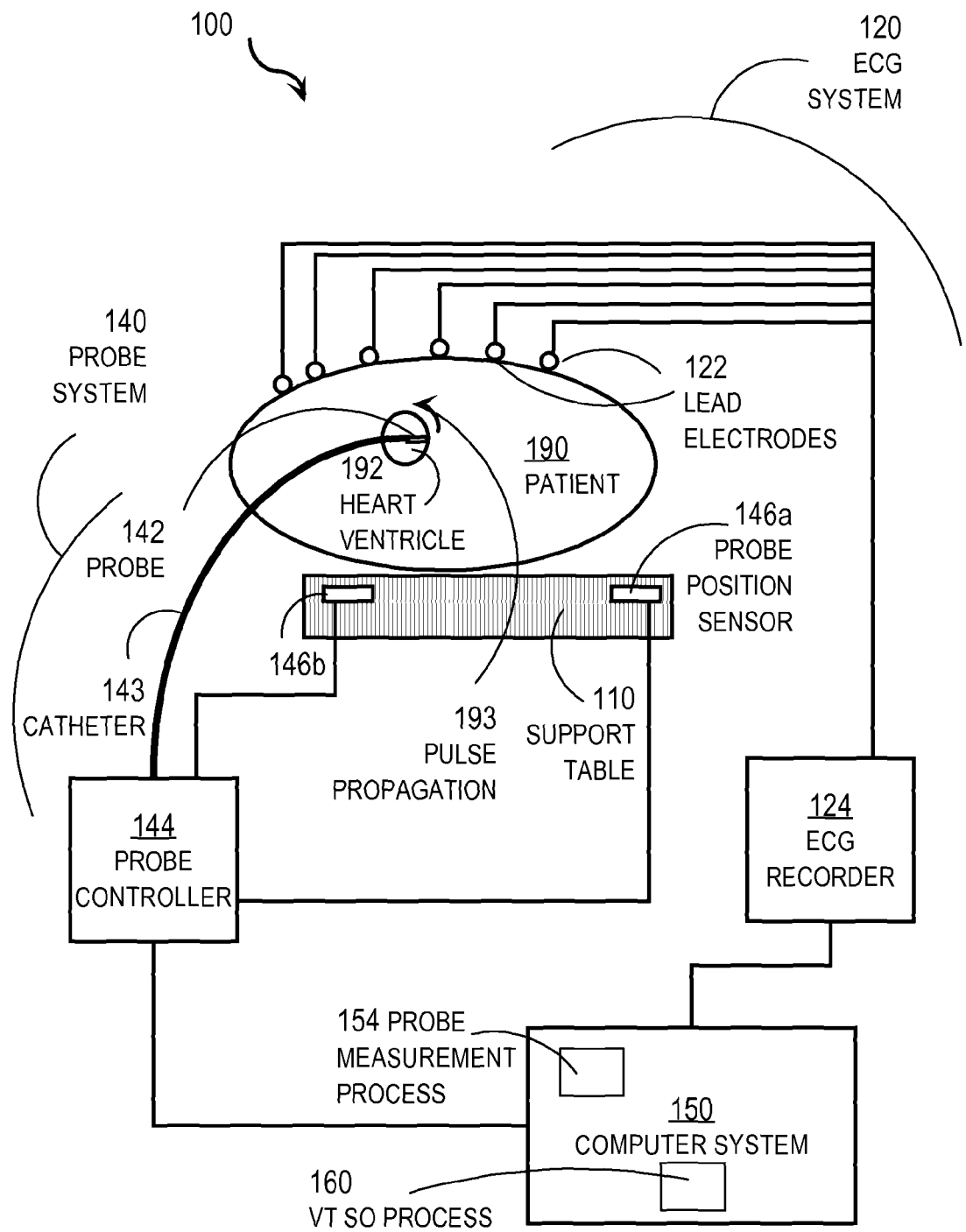
FIG. 1 is a block diagram that illustrates an example system for determining VT SO in a living subject, according to an embodiment.

FIG. 1 is a block diagram that illustrates an example system 100 for determining VT SO in a living subject. The system 100 includes an electrocardiograph (ECG) system 120, a probe system 140 and a computer system 150. The system 100 operates on a patient 190, who is a living subject, such as an animal or human. Although depicted for purposes of illustration, the patient 190 is not part of the system 100.

Like most ECG systems, ECG system 120 includes lead electrodes 122 that provide electrically conducting contact to a surface of a living body. The lead electrodes are connected by electrically conducting wires to an ECG recorder 124. The ECG recorder 124 records traces (on paper called electrocardiograms, or in digital files, or both) that indicate electrical signals received at or between the lead electrodes 122. A standard ECG system generates twelve traces, called leads, based on six uni-polar lead electrodes 122 and three bi-polar lead electrodes 122. A bipolar lead determines a difference in electrical voltage between two electrodes. By convention, a positive electrode is one in which the ECG records a positive (upward) deflection when the measured electrical impulse flows toward it and a negative (downward) deflection when it flows away from it. For a uni-polar lead, the electrical potential at an exploring electrode is compared to a reference point that averages electrical activity, rather than to that of another electrode. The single electrode of a uni-polar lead, termed the exploring electrode, is the positive electrode. In some embodiments, one or more steps of ECG recorder 124 are performed by an ECG process, not shown, on computer system 150.

The support table 110 supports the patient 190. The patient 190 includes a heart ventricle 192 part of a heart in the patient 190.

Probe system 140 includes a probe 142, a catheter 143 and a probe controller 144. In the illustrated embodiment, the probe system 140 includes probe position sensor 146a and probe position sensor 146b (collectively referenced hereinafter as probe positions sensors 146), and probe measurement process 154 on computer system 150.

The probe 142 is any device that is inserted into a living body for any reason, such as an ablating electrophysiological tip, well known in the art, for measuring voltage in the heart and generating lesions in the heart to change electrical conductance associated with arrhythmia. For example, the probe 142 is depicted in the heart ventricle 192 of patient 190. The probe 142 includes a probe electrode for introducing an electrical stimulation signal to tissue in contact with the probe electrode. An electrical pulse propagates from the probe in response to such a stimulation signal. For example, a direction of pulse propagation 193 as a result of a stimulation signal from probe 142 in contact with a wall of the heart ventricle 192 is depicted in FIG. 1.

The probe controller 144 is any device that is used to control operation of the probe, such as hand held manipulators that control the movement of the probe and control probe operations, such as stimulation, measurement and ablation.

The catheter 143 is a tube inserted into a lumen of the living subject, such as a blood vessel, through which the probe is passed to a particular location in the patient. Inside the catheter 143 are one or more control lines for connecting the probe to the probe controller 144. In other embodiments, the catheter is replaced by any tether that ties the probe to a device located outside the living subject and used to control the probe. In some embodiments the catheter is replaced by a wireless communication link between the probe 142 inside the patient and the probe controller 144 outside the patient.

In some embodiments, the probe system includes one or more probe positioning sensors, such as probe positioning sensors 146. Probe positioning sensors 146 determine the three dimensional position of probe 142 using any method known in the art, such as measuring strength of electromagnetic induction from an electrical source in the probe 142. A probe positioning process, such as a process executing on probe controller 144 or computer system 150, uses triangulation or other algorithms to deduce probe position from the measurements made at position sensors 146. Well known probe positioning systems for an electrophysiological catheter tip include CARTO™ provided by Biosense Webster, Inc. of Diamond Bar, Calif. and NAVX™ provided by St. Jude Medical of Sylmar, Calif.

A probe measurement process, such as probe measurement process 154 on computer system 150, determines conditions in patient 190 based on measurements made by probe 142. In some embodiments, probe measurement process 154 includes the probe positioning process, described above. For example, in some embodiments, probe measurement process 154 determines the action potential on an inner surface of the heart based on voltage measurements made over one or more heart cycles at probe 142, a probe position determined based on sensors 146, patient position (e.g., based on markers attached to the patient) and a model of the heart of patient 190 based on generic features or pre-operative internal scans of the patient. In some embodiments, such action potential is stored as a three dimensional (3D) electro-anatomic map of all or a portion of the heart and is presented as a colored area on a cartoon representation of a heart in a two dimensional screen image displayed to a human operator of probe controller 144. The probe position relative to the model heart is estimated using any of several estimation processes that are well known in the art.

According to an illustrated embodiment, a process 160 executing on computer system 150 combines information about current probe position and probe measurements, if any, from probe measurement process 154 with ECG data from ECG recorder 124 to determine VT SO with reference to the 3D electro-anatomic map of the heart wall (myocardium). Although process 154 is depicted on the same computer system 150 as the VT SO process 160 for purposes of illustration, in various other embodiments, one process executes on a different computer in communication with computer system 150, directly or indirectly via a communications or data network.

2.0 ECG Overview

Figure 2:
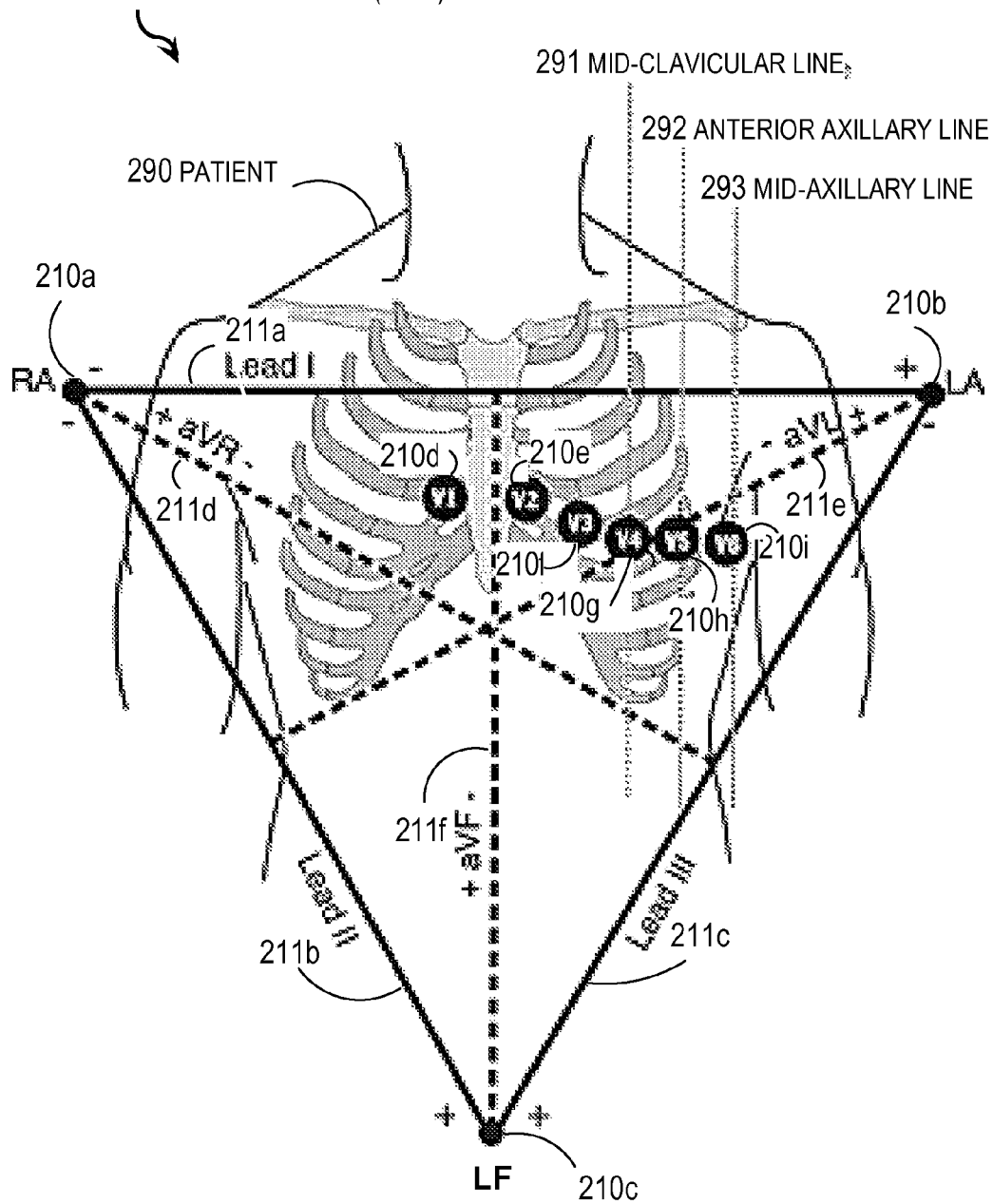
FIG. 2 is a block diagram that illustrates leads and placement of electrodes for standard electrocardiograph (ECG) measurements.

FIG. 2 is a block diagram that illustrates leads and placement of electrodes for standard electrocardiograph (ECG) measurements. For reference, a patient 290 is indicted by a drawing with a mid-clavicular line 291, an anterior axillary line 292 and a mid-axillary line 293. Electrodes for bipolar leads are placed at the upper right arm (RA) 210*a*, the upper left arm (LA) 210*b* and the left foot LF 210*c*. These same electrodes are also processed as uni-polar leads, as described below. Electrodes for uni-polar leads are placed at six locations on the chest indicated by V1 210*d*, V2 210*e*, V3 210*f*, V4 210*g* on mid-clavicular line 291, V5 210*h* on anterior axillary line 292 and V6 210*i* on the mid-axillary line 293. In some embodiments, the surface electrodes are placed as depicted in FIG. 2. In other embodiments, more or fewer electrodes are placed at zero or more of the positions depicted in FIG. 2.

The standard 12-lead ECG provides spatial information about the heart's electrical activity in 3 approximately orthogonal directions: patient right to left; patient head to toe (superior to inferior); and patient front to back (anterior to posterior). Bipolar lead I is based on the difference between electrode RA 210*a* and electrode LA 210*b*; and indicates the propagation 211*a* of pulses from patient right to left. Bipolar lead II is based on the difference between electrode RA 210*a* and electrode LF 210*c*; and indicates the propagation 211*b* of pulses from superior to inferior (with minor influence for right to left). Bipolar lead III is based on the difference between electrode LA 210*b* and electrode LF 210*c*; and indicates the propagation 211*c* of pulses from superior to inferior (with minor influence for left to right). Augmented uni-polar limb leads (frontal plane) are designated lead aVR, lead aVL and lead aVF; and, are based on average measurements at RA 210*a*, LA 210*b* and LF 210*c*. Lead aVR indicates the rightward propagation 211*d* of pulses perpendicular to lead III. Lead aVL indicates the leftward propagation 211*e* of pulses perpendicular to lead II. Lead aVF indicates the inferior-ward propagation 211*f* of pulses perpendicular to lead I. The positive uni-polar chest leads indicate propagation from the heart in a cross-sectional (horizontal) plane through the heart. Leads V1, V2, V3 from electrodes V1 210*d*, V2 210*e*, V3 210*f*, respectively, indicate propagation in the posterior to anterior direction (negative changes indicate the opposite direction). Leads V4, V5, V6 from electrodes V4 210*g*, V5 210*h*, V6 210*i*, respectively, indicate propagation in the lateral right to left direction (negative changes indicate the opposite direction).

Actual measurements at the standard 12 lead configuration of electrodes vary from patient to patient, depending on the location and direction of the electrical pulses inside the patient, and the size and location and electrical properties of the tissues in the patient.

In an ECG of a normal patient, heart beat (pulse rate) lies between 60 and 100 beats/minute. Rhythm is regular except for minor variations with respiration. A P-R interval is the time required for completion of aerial depolarization, conduction through the heart tissue, and arrival at the ventricular myocardial cells. The normal P-R interval is 0.12 to 0.20 seconds. The QRS interval represents the time required for ventricular cells to depolarize. The normal duration is 0.06 to 0.10 seconds. The Q-T interval is the time required for depolarization and repolarization of the ventricles. The time required is proportional to the heart rate. The faster the heart rate, the faster the repolarization, and therefore the shorter the Q-T interval. With slow heart rates, the Q-T interval is longer. The Q-T interval represents about 40% of the total time between the QRS complexes. In most cases, the Q-T interval lasts between 0.34 and 0.42 seconds.

Ventricular tissue is capable of spontaneous depolarization. When this occurs, a premature ventricular contraction (PVC) is initiated. Because the depolarization wave arises in the myocardium, it usually does not follow the normal path of ventricular depolarization. Therefore, the QRS complex is prolonged and unusual in shape. Ventricular Tachycardia (VT) is defined as a run of 3 or more PVCs.

To determine the source of VT, a probe is used to stimulate the heart once per heartbeat for one or more heartbeats at each of several locations in the ventricle of interest. This process is called pace-mapping. The 12-lead ECG of the VT is compared to each pace-mapped 12 lead ECG. When a match is found, it is determined that the stimulated site is the VT SO. When there is no match, however, there is no current process for determining where to stimulate next. It can take an electrophysiology tens to hundreds of pace-mapping locations and several hours to find the VT SO.

Figure 3:
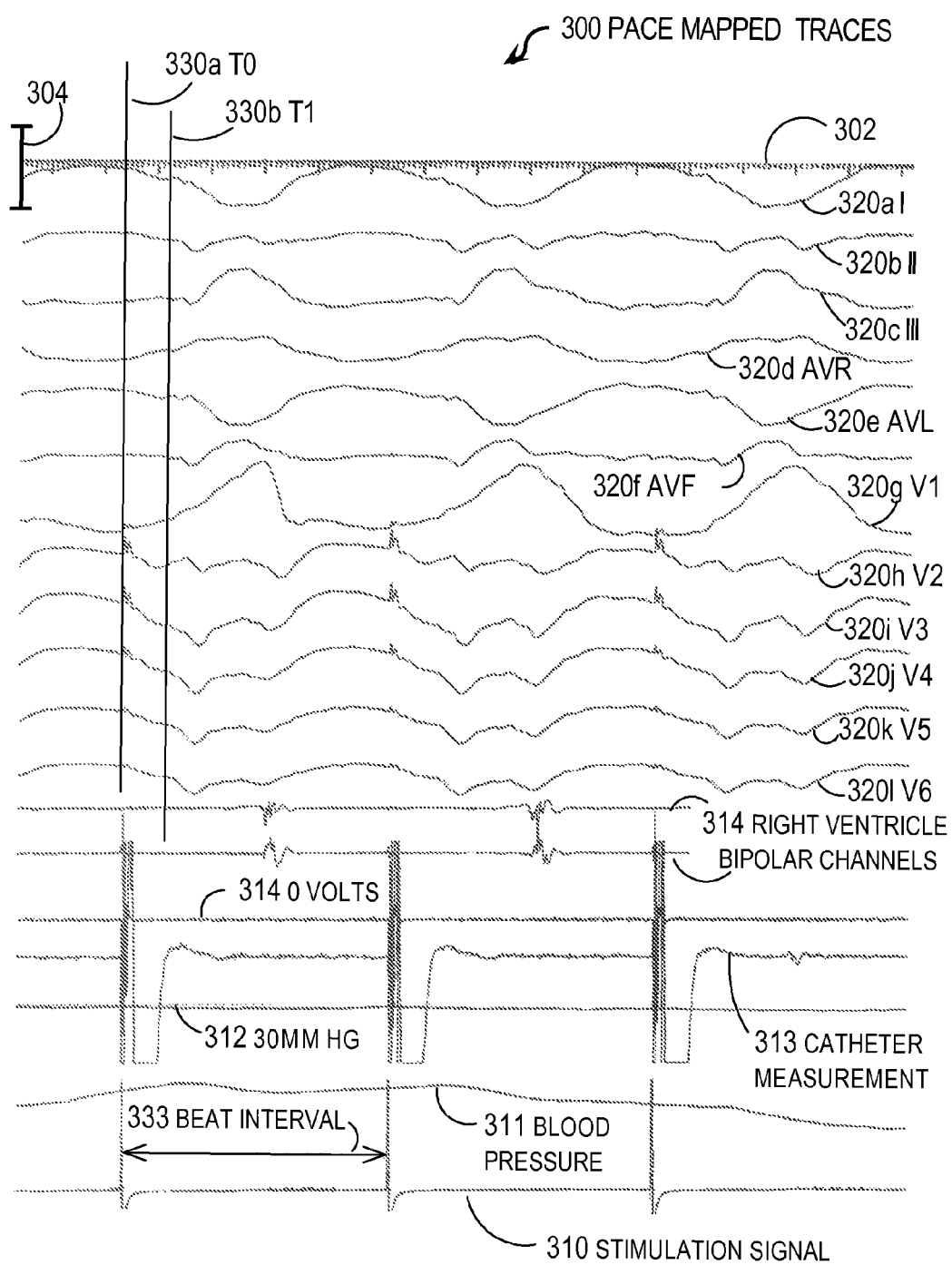
FIG. 3 is a graph that illustrates example stimulated signals for pace mapping a ventricle, according to an embodiment.

FIG. 3 is a graph that illustrates example stimulated signals for pace mapping a ventricle, according to an embodiment. The horizontal axis 302 indicates time, with the large tick marks separated by 0.1 seconds and the small tick marks by 0.01 seconds. FIG. 3 includes plots of multiple traces, each offset vertically by a different amount to avoid confusion, and all sharing the same horizontal time axis 302. Vertical axis 304 indicates the change in a measurable physical phenomenon, such as voltage, pressure, from some fixed value.

Trace 310, at the bottom, indicates a stimulation signal input to a probe, e.g., probe 142, to cause a depolarization at a location on a ventricle wall. The stimulation pulse is repeated at a rate indicated by beat interval 333.

Trace 311 indicates patient blood pressure during the stimulation. Horizontal line 312 provides a vertical origin for the blood pressure trace 311.

Trace 313 indicates electrical voltage measured at the probe tip, e.g. at the tip of probe 142. Horizontal Line 314 indicates a voltage measured at a proximal bipolar electrode. Trace 313 indicates that the ventricle wall is depolarized upon stimulation and then gradually reestablishes polarization after a few tenths of a second.

Traces 315 are the 2 local bipolar electrogram channels from the right ventricular chamber—a distal pair at the tip of the probe and a more proximal pair father up on the shaft of the catheter (e.g., on catheter 143 father from the probe 142).

The remaining traces indicate the 12 standard lead measurements. Traces 320*a*, 320*b*, 320*c*, 320*d*, 320*e*, 320*f*, 320*g*, 320*h*, 320*i*, 320*j*, 320*k*, 320*l* (collectively referenced hereinafter as traces 320) depicted voltage measurements at leads I, II, Ill, aVR, aVL, aVF, V1, V2, V3, V4, V5, V6, respectively, of a standard 12-lead ECG.

The time of the stimulated pulse is indicated by vertical line t0 330*a*. Also depicted is a time t1 330*b*, shortly after time t0 330*a*. In the illustrated embodiment, time t1 330*b* is 0.08 seconds after time t0 330*a*. It can be seen that in the interval from time t0 to time t1, some leads present a large increase in voltage (e.g., lead V1 320*g*), some leads present a large decrease in voltage (e.g., leads V2 320h, V3 320i and V4 320j) and some leads express little change (e.g., lead II 320b and lead aVF 320f).

Figure 4:
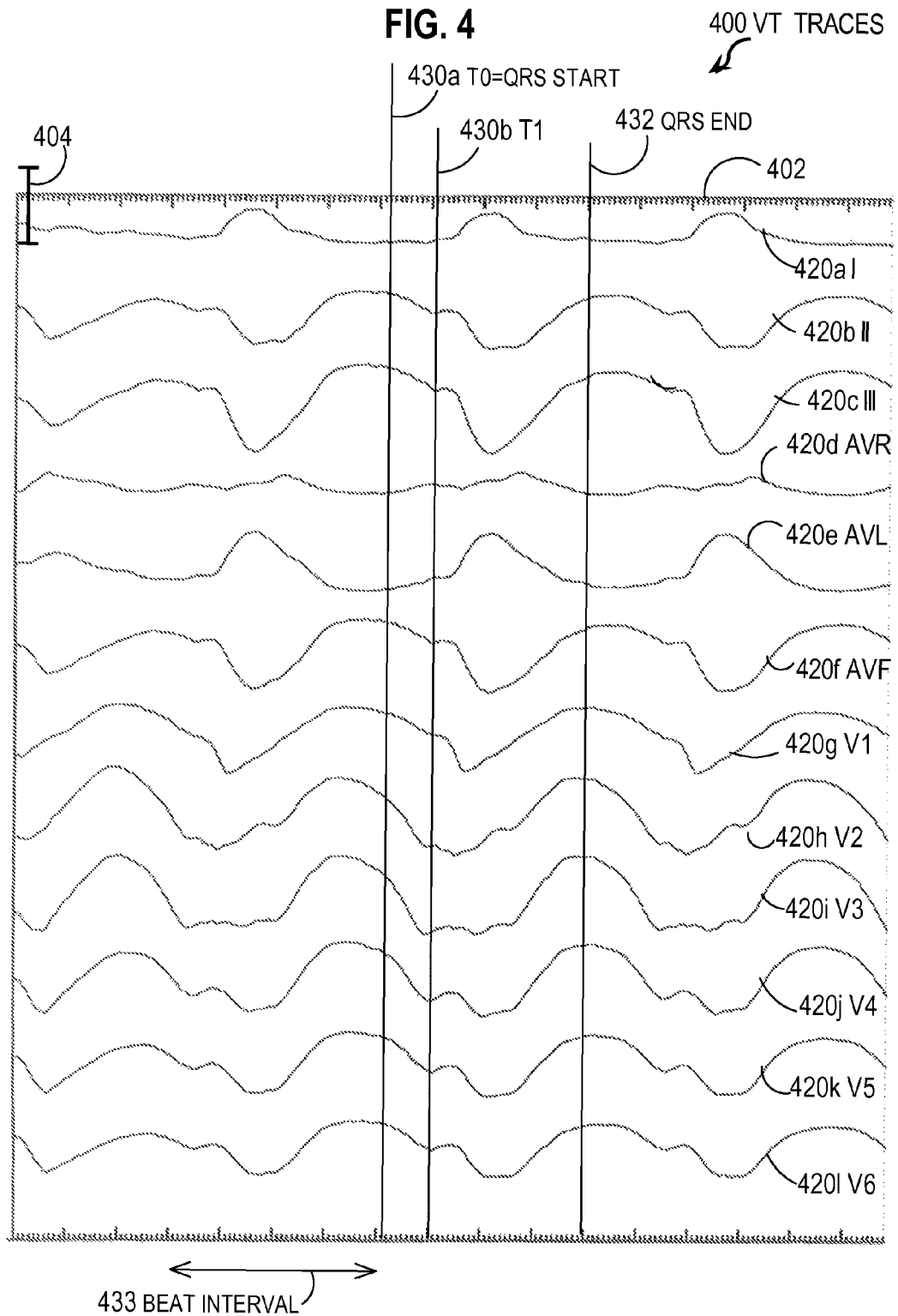
FIG. 4 is a graph that illustrates example measurements of a natural VT, according to an embodiment.

FIG. 4 is a graph that illustrates example measurements of a natural VT, according to an embodiment. The horizontal axis 402 indicates time, with the large tick marks separated by 0.1 seconds and the small tick marks by 0.01 seconds. FIG. 4 includes plots of multiple traces, each offset vertically by a different amount to avoid confusion, and all sharing the same horizontal time axis 402. Vertical axis 404 indicates the change in a measurable physical phenomenon, such as voltage, from some fixed value. The natural heart beat is indicated by beat interval 433.

The traces indicate the 12 standard lead measurements for the natural VT. Traces 420a, 420b, 420c, 420d, 420e, 420f, 420g, 420h, 420i, 420j, 420k, 420l (collectively referenced hereinafter as traces 420) depicted voltage measurements at leads I, II, III, aVR, aVL, aVF, V1, V2, V3, V4, V5, V6, respectively, of a standard 12-lead ECG.

The time of the QRS start is indicated by vertical line t0 430a. Also depicted is a time t1 430b, shortly after time t1 430a. In the illustrated embodiment, time t1 430b is 0.08 seconds after time t0 430a. It can be seen that in the interval from time t0 to time t1, some leads present a large increase in voltage (e.g., lead aVL 420e), some leads present a large decrease in voltage (e.g., leads aVF 420f, V2 420h and V3 420i) and some leads express little change (e.g., lead aVR 420d). These expressions differ at several leads from those expressed in FIG. 3.

Because the two 12-lead ECGs do not match, the site of the pace map for traces 320 is not the VT SO. There is no objective procedure in the prior art to determine where to move the probe to obtain a better match with the traces 420.

3.0 Method to Determine VT SO

According to embodiments of the invention, a site of origin of a natural electrical pulse inside a living body is derived from surface measurements of the natural pulse and multiple measurements of surface pulses from stimulated pulses at known locations. The three dimensional coordinates of the site of origin constitute three unknown quantities to be derived. Thus it is anticipated that at least three equations involving three known positions are useful in making the derivation. With additional equations involving additional known positions, uncertainty in the derived position can be reduced. Such solutions involve the minimization of square differences, called least-squares techniques. In an illustrated embodiment, digitized 12-lead ECG data of the induced VT and those created by pace-mapping at a number of distinct endocardial sites such as the left ventricular apex, inferior base, superior base, mid-septum and lateral wall of the ventricle are collected.

Figure 5:
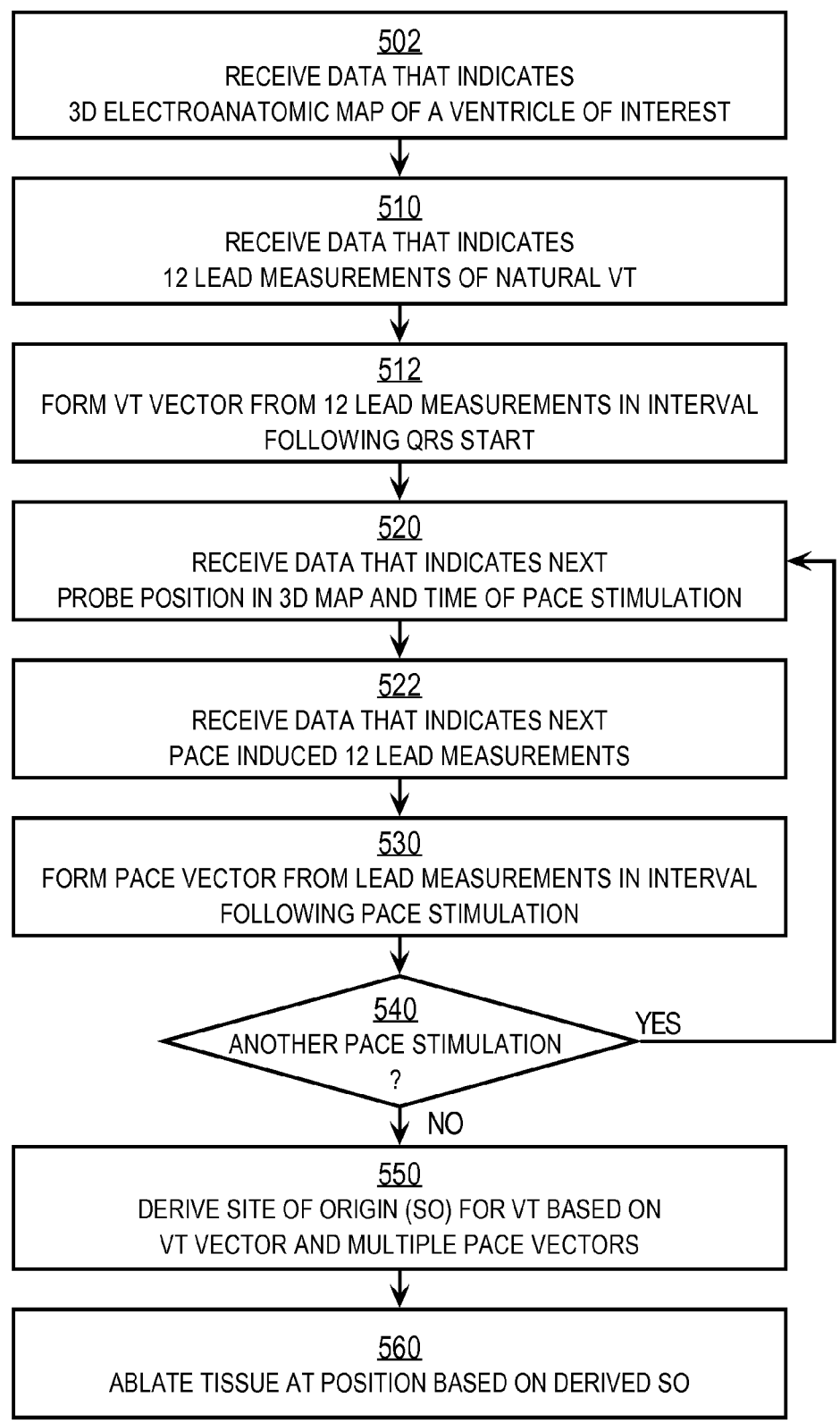
FIG. 5 is a flow diagram that illustrates at a high level a method for determining site of origin for VT, according to an embodiment.

FIG. 5 is a flow diagram that illustrates at a high level a method 500 for determining site of origin for VT, according to an embodiment. Although steps in FIG. 5 are shown in a particular order for purposes of illustration, in other embodiments, one or more steps may be performed in a different order or overlapping in time, in series or in parallel, or one or more steps may be omitted or added, or changed in some combination of ways. In other embodiments, a different site related to a different electrical pulse inside a living body is determined by a similar method.

In step 502, data is received that indicates a 3D electro-anatomic map of an organ of interest, such as a ventricle. Any method may be used to receive this data. For example, in various embodiments, the data is included as a default value in software instructions, is received as manual input from a network administrator on the local or a remote node, is retrieved from a local file or database, or is sent from a different node on the network, either in response to a query or unsolicited, or the data is received using some combination of these methods.

For example, during step 502, an interventional electrophysiologist executes multiple touches of a ventricle wall with probe 142, positioned by virtue of probe positioned sensors 146. This data is fed to a commercially available software package, such as CARTO™ or NAVX™ A model of a standard heart is combined with this data to determine the shape and polarization values of the particular ventricle 192 of particular patient 190. The result is the 3D electro-anatomic map of the ventricle of interest. In some embodiments, a different anatomical model is used for a different type of natural electrical pulse. In some embodiments, step 502 is omitted.

In step 510 data is received that indicates surface electrical measurements of the natural electrical pulse. For example, the 12 lead measurements associated with the natural VT are received, such as traces 420 depicted in FIG. 4.

In step 512 a natural vector is formed from the surface electrical measurements of the natural electrical pulse in a particular time interval. For example, a VT vector is formed from traces 420 in the time interval from t0 430a to t1 430b. The size of the time interval is selected to give a good indication of the direction of propagation of the pulse of interest. For example, in the case of a VT vector, the time interval starts at the start of the QRS interval, is a short time compared to the heart beat but sufficiently long to characterize the direction (positive or negative) and proximity of the pulse (as indicted by the magnitude of the measured voltage change). It is assumed for purposes of illustration that the time interval duration is 0.08 seconds. In other embodiments, other time interval durations are selected In the illustrated embodiment, a 12 element vector is produced based on the traces 420 and the time interval t0 430a to t1 430b. The first element of the vector is based on the direction and magnitude of the voltage change during the selected interval of the trace 420a of lead I by using a signed numeric value. Similarly, the second through 12th elements of the vector are based on the direction and magnitude of the voltage change during the selected interval of the traces 420b through 420l, respectively. For purposes of illustration it is assumed that the VT vector is a 12 element vector represented by the twelve values (0, −2, −2, 0, 1, −1, −1, −2, −2, −2, −1, −1), based on the changes in the selected 0.08 second intervals beginning at the start of QRS.

This vector captures the propagation of a surface pulse that is based on the propagation of the natural pulse inside the living body. In some embodiments, the 12 element vector is reduced to a 3 element vector in the patient coordinate system (right to left, superior to inferior, anterior to posterior).

In some embodiments that involve periodic pulses, such as in a beating heart, each vector element is based on the average of several time intervals all during the same phase of multiple periodic pulses. Thus, each of the twelve values in the illustrated VT vector represents the average change over 0.08 seconds after QRS onset for several heart beats. Averaging serves to increase signal to noise ratio and produce vectors that are more stable in time.

In some embodiments, the change is determined by the signed temporal gradient over the selected interval (e.g., in milliVolts per millisecond). In some embodiments, more than one statistic of the change during the selected interval is characterized, such as both the signed gradient and signed curvature of the change in the selected interval. In this case the vector has twice as many elements, e.g., 24 instead of 12.

As further statistics of the change are characterized, the number of elements in the vector increases.

In some embodiments, not all lead traces are used. For example, in some embodiments leads I, II and III are excluded and the vector includes only 9 elements, one for each electrode.

Figure 6:
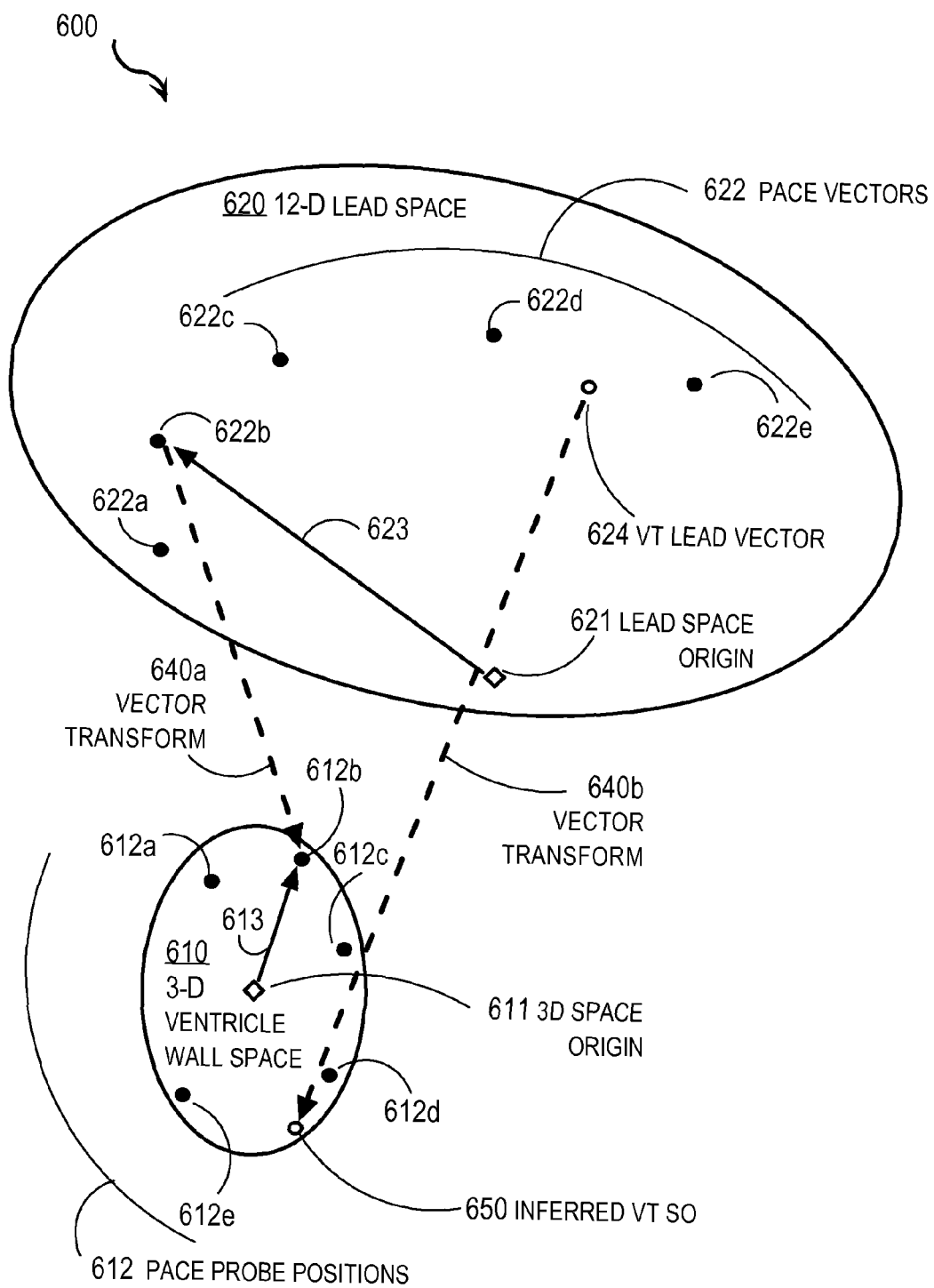
FIG. 6, is a block diagram that illustrates example mapping of vectors produced from lead measurements to positions in a ventricle, according to an embodiment.

FIG. 6 is a block diagram 600 that illustrates example mapping of vectors produced from lead measurements to positions in a ventricle, according to an embodiment. Diagram 600 includes an ellipse that represents 12 dimensional lead space 620 and a second ellipse that represents 3 dimensional ventricle wall space 610. The origin 611 of the 3-D ventricle wall space is represented by the center of the diamond inside 3-D space 610. Locations in the ventricle are represented by points in this ellipse, such as point 612a, point 612b, point 612c, point 612d, point 612d, point 612e, inferred VT SO point 650, among others, collectively referenced hereinafter as ventricle space points 612. The origin 621 of the 12-D lead space is represented by the center of the diamond inside 3-D space 620. Particular lead measurements are represented by points in this ellipse, such as point 622a, point 622b, point 622c, point 622d, point 622d, point 622e, and VT lead vector point 624, among others, collectively referenced hereinafter as ventricle space points 622. Each dimension in lead space corresponds to a different lead of the 12 standard ECG leads.

A point in each space can also be represented by an arrow that starts at the origin and ends at the point. For example, point 612b can be represented by the arrow 613 from the origin 611 to the point 612b. The point 622b can be represented by the arrow from the origin 621 to the point 622b.

It is assumed for purposes of illustration that the VT vector (0, −2, −2, 0, 1, −1, −1, −2, −2, −2, −1, −1), formed during step 512, is represented by the VT lead vector point 624.

In step 520, data is received that indicates the next position of a stimulating probe and the time of the stimulation. For example, during step 520 the location is received of the tip of probe 142 in ventricle 192 as expressed in the coordinates of the 3D electro-anatomic model received in step 502. It is further assumed that this position corresponds to point 612a in the 3-D ventricle wall space 610

In step 522, data is received that indicates surface electrical measurements of the stimulation. For example, during step 522, an interventional electrophysiologist moves the probe 142 to the depicted position in the heart ventricle 192 and depolarizes the ventricle wall. The 12 lead measurements associated with the pace mapping are received, such as traces 320 depicted in FIG. 3.

In step 530 a stimulated vector is formed from the surface electrical measurements of the stimulation in a particular time interval. The vector elements are formed in the same manner as the elements of the natural pulse vector is formed, from the same surface electrical sensors at the same locations. The size of the time interval is selected to match that used to form the natural pulse vector. For example, a pace vector is formed from 12 traces 320 in the time interval from t0 330a to t1 330b. It is assumed for purposes of illustration that the time interval duration is 0.08 seconds. In other embodiments, other time interval durations are selected In the illustrated embodiment, a 12 element vector is produced based on the traces 320 and the time interval t0 330a to t1 330b. For purposes of illustration it is assumed that the VT vector is a 12 element vector represented by the twelve values (−1, 0, 0, 1, −1, 0, 2, −2, −2, −2, −1, −1), based on the changes in the selected 0.08 second interval beginning at the stimulation voltage spike.

This vector captures the propagation of a surface pulse that is based on the propagation of the stimulated pulse inside the living body. In some embodiments, the 12 element vector is reduced to a 3 element vector in the patient coordinate system (right to left, superior to inferior, anterior to posterior).

In some embodiments that involve periodic pulses, such as in a beating heart, each vector element is based on the average of several time intervals all during the same phase of multiple periodic pulses. Thus, each of the twelve values in the vector represents the average change over 0.08 seconds after the stimulation spike for several stimulated heart beats. In some embodiments, more or fewer vector elements are determined to match the vector elements in the natural pulse vector.

In step 540, it is determined whether another pace stimulation is to be performed. If so, control passes back to step 520 to receive data that indicates the time and location of the next stimulation signals. For purposes of illustration, it is assumed that steps 520 through 540 are repeated sufficiently to have enough information to deduce the 3D position of the site of origin.

For purposes of illustration, it is assumed that steps 520 through 540 are repeated five times. As a result of repeating these steps five times, five 12-D vectors are obtained, represented by point 622a, point 622b, point 622c, point 622d, point 622e in FIG. 6. Associated with each is a 3-D position on a wall of the ventricle of interest, where depolarization pulses were stimulated, represented by point 612a, point 612b, point 612c, point 612d and point 612e, respectively.

In step 550 a site of origin is determined based on the natural vector and the multiple stimulated vectors with associated locations. Any method may be used. For example, inferred VT SO 650 is determined based on the associated points (point 622a associated with point 612a; point 622b associated with point 612b; point 622c associated with point 612c; point 622d associated with point 612d; point 622e associated with point 612e) and the VT lead vector 624.

In some embodiments, a single vector transform is determined that best converts every stimulated vector to the different corresponding position within the body. Any method may be used to determine the transform. In some embodiments, an electrical propagation model is used to produce a model of surface electrical values tied to a site of origin and parameters that describe electrical properties of intervening tissues. In some embodiments, a parametric equation of a particular or arbitrary polynomial or other form is used to relate the 12-D vectors to the 3-D vectors. The parameters of the propagation model or arbitrary form are fit to the observations of surface electrical quantities, for example using a least squares approach in some embodiments.

When the vector transform operates on any 12-D vector used in its derivation, the output is a 3-D vector that is close to the associated 3-D point. Thus when the vector transom operates on point 622b it outputs a 3-D coordinate close to 612b, as represented by the arrow 640a. The same vector transform operates on VT lead vector 624 to produce an inferred VT SO point 650, as represented by arrow 640b.

In some embodiments a linear combination of the different stimulated vectors is determined to produce the natural vector. For example, a linear combination of the vectors represented by points 622a, 622b, 622c, 622d, 622e, is determined that produces the VT lead vector 624. That same linear combination is used to deduce the inferred VT SO point 650 from the 3-D positions represented by points 612a, 612b, 612c, 612d, 612e. In essence, the vectors 622a through 622e form a vector basis set for describing any arbitrary point in 12-D space 620, while the corresponding vectors 612a through 612e form a basis set for describing any point in 3-D space 610.

In some embodiments, inferred VT SO point 650 is taken as the final VT SO and control passes to step 560. In some embodiments, the inferred VT SO point 650 is used as the next stimulation location and control passes back to step 520.

In some embodiments, a 3-dimensional (3D) vector is derived from the VT 12-lead ECG as well as from each of the pace-map 12-lead ECGs. A quantitative comparison between the 3D vector derived from the VT and those vectors derived from the pace-maps is used to guide the catheter movement to the SO of VT. In some embodiments, vector analysis is used to determine an angle between the pace-map-derived vector and the VT-derived vector.

In some embodiments, paired analysis of each of the created pace-map-derived vectors with the VT-derived vector provide multiple correction angles, resulting in a final direction for a vector that intersects with the surface grid of the previously created electro-anatomic map. For example, an angle formed between arrow 623 and arrow 640a is the vector transform. In some embodiments, an angle formed between arrow 623 and arrow 613 is the vector transform. That same angle is applied to a vector from origin 621 to VT lead vector point 624 to produce the derived vector (transform 640b). The derived vector (transform 640b) intersects with the 3D electro-anatomic map at a minimum of one and a maximum of two points, including point 650. In the case of two intersection points, one of the points is rejected based upon data derived from concurrent paired analyses. The result is the identification of a single point (e.g., inferred VT SO point 650) which represents the predicted VT SO. In some embodiments, the probe is directed to the next pacing site by on-line vector analysis and the VT SO is inferred with subsequent iterations, when enough data has been acquired.

As mentioned above, in some embodiments, validation by pace-mapping at that specific point and its immediate vicinity confirms this point as the SO of VT. Using this method, one can rapidly focus on a specific site rather than performing extensive, time-consuming pace-mapping throughout the ventricle in search of the SO of VT.

In some embodiments, the least squares method is also used to find the least distance between two vectors thus detecting vector coincidence of the VT-derived vector and the pace-map-derived vectors. This is used as an adjunct technique either as an initial step to align the VT-derived vector with one of the pace-map-derived vectors to guide subsequent vector analysis or after completion of vector analysis to further qualify the predicted VT SO, where one is dealing with a much more circumscribed area, for more accurate VT SO localization If it is determined, in step 540, that another pace stimulation is not to be performed, control passes to step 560. In step 560, treatment is administered based on the site of origin. For example, the VT SO is ablated with electrical, chemical or other source of energy to form a lesion that inhibits depolarization at the location of that lesion.

4. Hardware Overview

Figure 7:
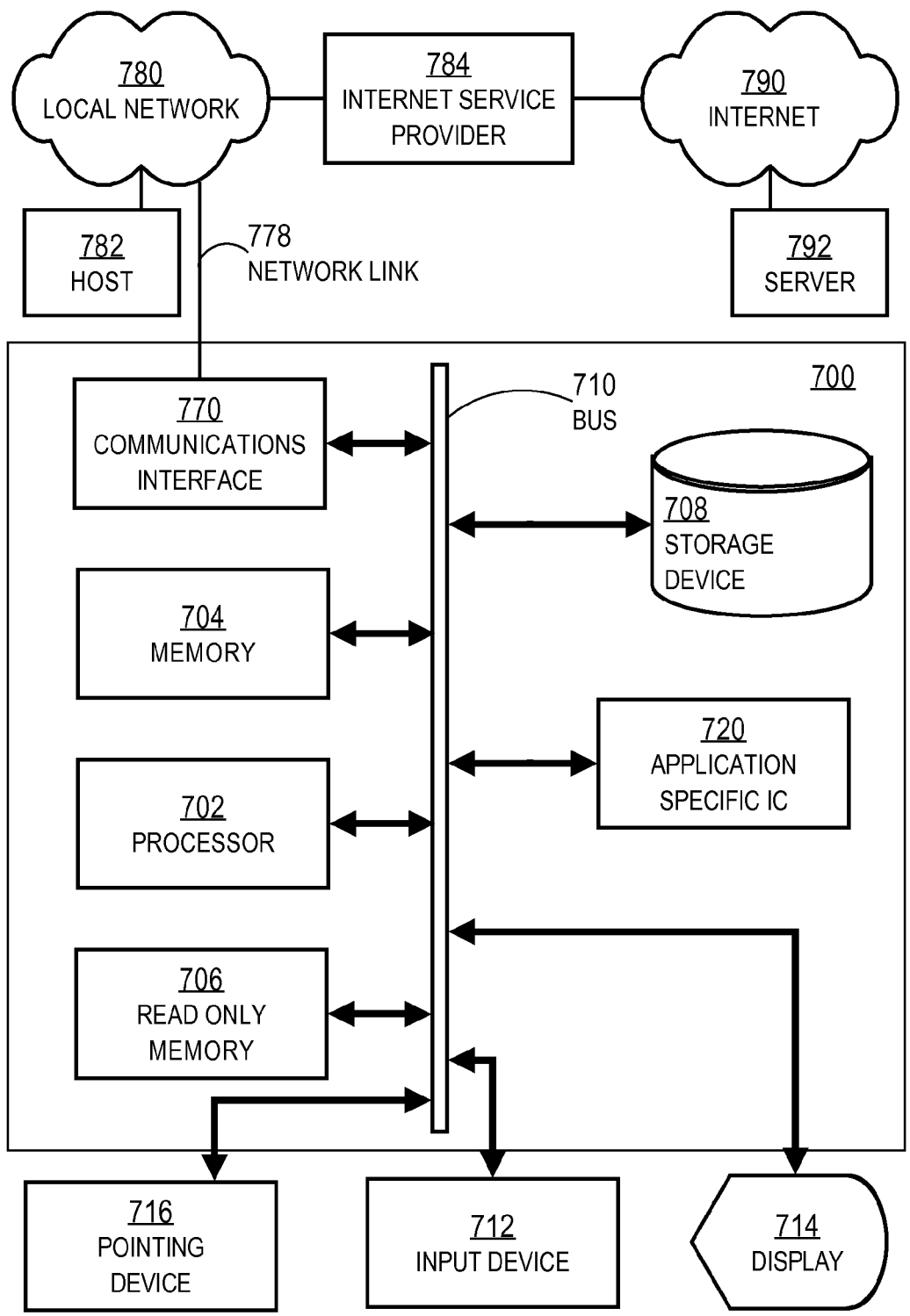
FIG. 7 is a block diagram that illustrates a computer system upon which an embodiment of the invention may be implemented.

FIG. 7 is a block diagram that illustrates a computer system 700 upon which an embodiment of the invention may be implemented. Computer system 700 includes a communication mechanism such as a bus 710 for passing information between other internal and external components of the computer system 700. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 710 includes many parallel conductors of information so that information is transferred quickly among devices coupled to the bus 710. One or more processors 702 for processing information are coupled with the bus 710. A processor 702 performs a set of operations on information. The set of operations include bringing information in from the bus 710 and placing information on the bus 710. The set of operations also typically include comparing two or more units of information, shifting positions of units of information, and combining two or more units of information, such as by addition or multiplication. A sequence of operations to be executed by the processor 702 constitutes computer instructions.

Computer system 700 also includes a memory 704 coupled to bus 710. The memory 704, such as a random access memory (RAM) or other dynamic storage device, stores information including computer instructions. Dynamic memory allows information stored therein to be changed by the computer system 700. RAM allows a unit of information stored at a location called a memory address to be stored and retrieved independently of information at neighboring addresses. The memory 704 is also used by the processor 702 to store temporary values during execution of computer instructions. The computer system 700 also includes a read only memory (ROM) 706 or other static storage device coupled to the bus 710 for storing static information, including instructions, that is not changed by the computer system 700. Also coupled to bus 710 is a non-volatile (persistent) storage device 708, such as a magnetic disk or optical disk, for storing information, including instructions, that persists even when the computer system 700 is turned off or otherwise loses power.

Information, including instructions, is provided to the bus 710 for use by the processor from an external input device 712, such as a keyboard containing alphanumeric keys operated by a human user, or a sensor. A sensor detects conditions in its vicinity and transforms those detections into signals compatible with the signals used to represent information in computer system 700. Other external devices coupled to bus 710, used primarily for interacting with humans, include a display device 714, such as a cathode ray tube (CRT) or a liquid crystal display (LCD), for presenting images, and a pointing device 716, such as a mouse or a trackball or cursor direction keys, for controlling a position of a small cursor image presented on the display 714 and issuing commands associated with graphical elements presented on the display 714.

In the illustrated embodiment, special purpose hardware, such as an application specific integrated circuit (IC) 720, is coupled to bus 710. The special purpose hardware is configured to perform operations not performed by processor 702 quickly enough for special purposes. Examples of application specific ICs include graphics accelerator cards for generating images for display 714, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 700 also includes one or more instances of a communications interface 770 coupled to bus 710. Communication interface 770 provides a two-way communication coupling to a variety of external devices that operate with their own processors, such as printers, scanners and external disks. In general the coupling is with a network link 778 that is connected to a local network 780 to which a variety of external devices with their own processors are connected. For example, communication interface 770 may be a parallel port or a serial port or a universal serial bus (USB) port on a personal computer. In some embodiments, communications interface 770 is an integrated services digital network (ISDN) card or a digital subscriber line (DSL) card or a telephone modem that provides an information communication connection to a corresponding type of telephone line. In some embodiments, a communication interface 770 is a cable modem that converts signals on bus 710 into signals for a communication connection over a coaxial cable or into optical signals for a communication connection over a fiber optic cable. As another example, communications interface 770 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 770 sends and receives electrical, acoustic or electromagnetic signals, including infrared and optical signals, that carry information streams, such as digital data.

The term computer-readable medium is used herein to refer to any medium that participates in providing information to processor 702, including instructions for execution. Such a medium may take many forms, including, but not limited to, non-volatile media, volatile media and transmission media. Non-volatile media include, for example, optical or magnetic disks, such as storage device 708. Volatile media include, for example, dynamic memory 704. Transmission media include, for example, coaxial cables, copper wire, fiber optic cables, and waves that travel through space without wires or cables, such as acoustic waves and electromagnetic waves, including radio, optical and infrared waves.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 778 typically provides information communication through one or more networks to other devices that use or process the information. For example, network link 778 may provide a connection through local network 780 to a host computer 782 or to equipment 784 operated by an Internet Service Provider (ISP). ISP equipment 784 in turn provides data communication services through the public, world-wide packet-switching communication network of networks now commonly referred to as the Internet 790. A computer called a server 792 connected to the Internet provides a service in response to information received over the Internet. For example, server 792 provides information representing video data for presentation at display 714.

The invention is related to the use of computer system 700 for implementing the techniques described herein. According to one embodiment of the invention, those techniques are performed by computer system 700 in response to processor 702 executing one or more sequences of one or more instructions contained in memory 704. Such instructions, also called software and program code, may be read into memory 704 from another computer-readable medium such as storage device 708. Execution of the sequences of instructions contained in memory 704 causes processor 702 to perform the method steps described herein. In alternative embodiments, hardware, such as application specific integrated circuit 720, may be used in place of or in combination with software to implement the invention. Thus, embodiments of the invention are not limited to any specific combination of hardware and software.

The signals transmitted over network link 778 and other networks through communications interface 770, carry information to and from computer system 700. Computer system 700 can send and receive information, including program code, through the networks 780, 790 among others, through network link 778 and communications interface 770. In an example using the Internet 790, a server 792 transmits program code for a particular application, requested by a message sent from computer 700, through Internet 790, ISP equipment 784, local network 780 and communications interface 770. The received code may be executed by processor 702 as it is received, or may be stored in storage device 708 or other non-volatile storage for later execution, or both. In this manner, computer system 700 may obtain application program code in the form of a signal on a carrier wave.

Various forms of computer readable media may be involved in carrying one or more sequence of instructions or data or both to processor 702 for execution. For example, instructions and data may initially be carried on a magnetic disk of a remote computer such as host 782. The remote computer loads the instructions and data into its dynamic memory and sends the instructions and data over a telephone line using a modem. A modem local to the computer system 700 receives the instructions and data on a telephone line and uses an infra-red transmitter to convert the instructions and data to a signal on an infra-red a carrier wave serving as the network link 778. An infrared detector serving as communications interface 770 receives the instructions and data carried in the infrared signal and places information representing the instructions and data onto bus 710. Bus 710 carries the information to memory 704 from which processor 702 retrieves and executes the instructions using some of the data sent with the instructions. The instructions and data received in memory 704 may optionally be stored on storage device 708, either before or after execution by the processor 702.

5.0 Extensions and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for determining a site of origin of a natural electrical pulse in a living body comprising:
   determining a first vector of temporal changes in electrical data measured at a plurality of electrical sensors positioned at a corresponding plurality of locations on an external surface of a living body due to a natural electrical pulse, wherein each vector comprises a plurality of properties of the temporal changes at each electrical sensor;
   determining a different vector of temporal changes in electrical data measured at the plurality of electrical sensors positioned at the corresponding plurality of locations on the external surface of the living body due to each stimulated signal of a plurality of stimulated signals within the living body, wherein each vector comprises a plurality of properties of the temporal changes at each electrical sensor;

receiving stimulated position data that indicates a different corresponding position within the living body where each of the plurality of stimulated signals originates; and determining the site of origin of the natural electrical pulse based on the first vector and the plurality of different vectors and the stimulated position data.

2. A method as recited in claim 1, wherein the natural electrical pulse is a ventricular tachycardia arrhythmia.

3. A method as recited in claim 1, wherein the electrical data measured at the plurality of electrical sensors positioned at the corresponding plurality of locations on a surface of the living body comprises electrocardiograph (ECG) lead data for a plurality of ECG leads positioned at three or more of twelve standard ECG positions.

4. A method as recited in claim 1, wherein:
said step of determining the first vector of temporal changes further comprising determining a change in voltage at each lead of at least three leads of an ECG system during a first time interval after onset of an electrical depolarization of heart ventricles known as a QRS portion of a heartbeat; and
said step of determining the different vector of temporal gradients further comprising determining a change in voltage at each lead of the at least three leads of the ECG system during the first time interval after stimulation by a catheter positioned inside a heart ventricle of interest.

5. A method as recited in claim 1, further comprising, after said step of determining the site of origin of the natural electrical pulse, applying treatment to the site of origin.

6. A method as recited in claim 1, further comprising, before said step of determining the site of origin of the natural pulse, receiving data that indicates a three-dimensional electro-anatomic map of a ventricle of interest.

7. A method as recited in claim 1, said step of determining the different vector of temporal changes further comprising, for each stimulation signal of the plurality of stimulation signals:
positioning a electrophysiological catheter at a different corresponding position in the living body; and
discharging a stimulation signal with a spike in voltage of a particular amplitude repeated at a particular rate.

8. A method as recited in claim 7, wherein
the different corresponding position in the living body is a different particular position on a wall of a ventricle of a heart; and
the particular rate is a repeat rate of a ventricular tachycardia arrhythmia.

9. A method as recited in claim 1, said step of determining the site of origin of the natural electrical pulse further comprising determining a single vector transform that best converts every different vector to the different corresponding position within the body.

10. A method as recited in claim 1, said step of determining the site of origin of the natural electrical pulse further comprising determining a linear combination of the different vectors to produce the first vector.

11. A method as recited in claim 10, said step of determining the site of origin of the natural electrical pulse further comprising applying the linear combination to the corresponding positions to determine the site of origin.

12. A non-transitory computer-readable medium carrying one or more sequences of instructions for determining site of origin or a natural electrical pulse inside a living body, wherein execution of the one or more sequences of instructions by one or more processors causes the one or more processors to perform the steps of:
determining a first vector of temporal changes in electrical data measured at a plurality of electrical sensors positioned at a corresponding plurality of locations on an external surface of a living body due to a natural electrical pulse, wherein each vector comprises a plurality of properties of the temporal changes at each electrical sensor;
determining a different vector of temporal changes in electrical data measured at the plurality of electrical sensors positioned at the corresponding plurality of locations on the external surface of the living body due to each stimulated signal of a plurality of stimulated signals within the living body, wherein each vector comprises a plurality of properties of the temporal changes at each electrical sensor;
receiving stimulated position data that indicates a different corresponding position within the living body where each of the plurality of stimulated signals originates; and
determining the site of origin of the natural electrical pulse based on the first vector and the plurality of different vectors and the stimulated position data.

13. A system for determining a site of origin of a natural electrical pulse in a living body comprising:
means for determining a first vector of temporal changes in electrical data measured at a plurality of electrical sensors positioned at a corresponding plurality of locations on an external surface of a living body due to a natural electrical pulse, wherein each vector comprises a plurality of properties of the temporal changes at each electrical sensor;
means for determining a different vector of temporal changes in electrical data measured at the plurality of electrical sensors positioned at the corresponding plurality of locations on the external surface of the living body due to each stimulated signal of a plurality of stimulated signals within the living body, wherein each vector comprises a plurality of properties of the temporal changes at each electrical sensor;
means for receiving stimulated position data that indicates a different corresponding position within the living body where each of the plurality of stimulated signals originates; and
means for determining the site of origin of the natural electrical pulse based on the first vector and the plurality of different vectors and the stimulated position data.

* * * * *